United States Patent
Inoue et al.

(10) Patent No.: US 7,713,391 B2
(45) Date of Patent: May 11, 2010

(54) METHOD AND APPARATUS FOR DIAGNOSING AN ABNORMALITY OF A GAS-CONCENTRATION MEASURING APPARATUS

(75) Inventors: Yoshinori Inoue, Kasugai (JP); Hiroshi Inagaki, Komaki (JP); Norikazu Ieda, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 962 days.

(21) Appl. No.: 11/316,809

(22) Filed: Dec. 27, 2005

(65) Prior Publication Data

US 2006/0157348 A1 Jul. 20, 2006

(30) Foreign Application Priority Data

Dec. 28, 2004 (JP) ............................ P2004-381746
Dec. 15, 2005 (JP) ............................ P2005-362182

(51) Int. Cl.
*G01N 27/41* (2006.01)

(52) U.S. Cl. ........................ 204/401; 204/424; 204/427; 123/688

(58) Field of Classification Search .................. 204/401
See application file for complete search history.

(56) References Cited

U.S. PATENT DOCUMENTS

| | | | | |
|---|---|---|---|---|
| 5,392,643 A | * | 2/1995 | O'Kennedy et al. ...... | 73/114.73 |
| 5,513,522 A | | 5/1996 | Seki et al. | |
| 6,136,169 A | * | 10/2000 | Okamoto ..................... | 204/401 |
| 6,164,125 A | * | 12/2000 | Kawase et al. ........... | 73/114.73 |
| 6,343,499 B1 | | 2/2002 | Inagaki et al. | |
| 7,142,976 B2 | * | 11/2006 | Inoue et al. .................. | 701/114 |
| 2004/0000493 A1 | * | 1/2004 | Yasui et al. .................. | 205/775 |
| 2004/0025856 A1 | * | 2/2004 | Iida et al. ..................... | 123/688 |
| 2004/0099528 A1 | * | 5/2004 | Hattori ........................ | 204/401 |
| 2004/0222094 A1 | * | 11/2004 | Ieda et al. .................... | 204/424 |

FOREIGN PATENT DOCUMENTS

JP 11-107830 4/1999

\* cited by examiner

*Primary Examiner*—Harry D Wilkins, III
*Assistant Examiner*—Bryan D. Ripa
(74) *Attorney, Agent, or Firm*—Sughrue Mion, PLLC

(57) ABSTRACT

In an activation state of a sensor device, when voltage on the connection points between the sensor device and the sensor control circuit becomes a preset abnormal value, electric cut off is made between the sensor control circuit and the connection point. Then, the delivery of power to the heater is ceased to lower the temperature of the cells to a below of an activation temperature, thereby increasing the internal resistance of the cell. Thereafter, the sensor control circuit supplies to the sensor device a current in a degree not to damage the sensor device, to detect voltages on the connection points at that time. By comparing between the voltages on the respective connection points detected, a content and location of abnormality occurred is identified for the sensor device.

4 Claims, 5 Drawing Sheets

FIG. 3

| MODE | SWITCH | | | | | | |
|---|---|---|---|---|---|---|---|
| | SW1 | SW2 | SW3 | SW4 | SW5 | SW6 | SW7 |
| GAS-CONCENTRATION MEASURING MODE | OFF | ON | ON | OFF | ON | ON | ON |
| PROTECTION MODE | OFF | OFF | OFF | OFF | OFF | OFF | OFF |
| ABNORMALITY DIAGNOSTIC MODE | ON | OFF | OFF | ON | OFF | ON | ON |

FIG. 4

| ABNORMAL NODE | TERMINAL | IDENTIFYING CONDITION |
|---|---|---|
| GND SHORT | Vs+ | VOLTAGE Vs+ < VOLTAGE COM, AND VOLTAGE Vs+ < VOLTAGE Ip+ |
| | COM | OTHER CASES THAN UPPER/LOWER |
| | Ip+ | VOLTAGE Ip+ < VOLTAGE COM, AND VOLTAGE Ip+ < VOLTAGE Vs+ |
| VB SHORT | Vs+ | VOLTAGE Vs+ > VOLTAGE COM, AND VOLTAGE Vs+ > VOLTAGE Ip+ |
| | COM | OTHER CASES THAN UPPER/LOWER |
| | Ip+ | VOLTAGE Ip+ > VOLTAGE COM, AND VOLTAGE Ip+ > VOLTAGE Vs+ |

METHOD AND APPARATUS FOR DIAGNOSING AN ABNORMALITY OF A GAS-CONCENTRATION MEASURING APPARATUS

BACKGROUND OF THE INVENTION

1. Field of the Invention

The present invention relates to a method and apparatus for diagnosing an abnormality of a gas-concentration measuring apparatus.

2. Description of the Related Art

In the related art, in combustion control of internal combustion engines including gasoline engines, there is known a combustion control scheme that the delivery of fuel, in amount, is placed under feedback control responsively to a concentration of a predetermined portion of the exhaust gas by controlling the air/fuel ratio of a mixture gas of the air and fuel to be delivered to the internal combustion engine, in order to reduce the CO, NOx and HC in the exhaust gas.

As a gas sensor for use in control of such air/fuel ratio, there are known an oxygen sensor arranged with cells having electrodes on both surfaces of a solid electrolyte based on zirconia or the like in a manner one electrode being exposed to a sample gas and the other electrode to the air so that the sample gas can be measured its gas concentration by a potential difference caused between the sample gas and the air, a full-range air/fuel ratio sensor (also termed a UEGO sensor) arranged with two cells having electrodes on the both surface of a solid electrolyte in a manner sandwiching a measurement chamber so that the sample gas can be detected its oxygen concentration over from a rich to lean range by introducing the sample gas into the measurement chamber through a diffusion resistance member, and a NOx sensor arranged to measure a gas content of NOx by additionally providing another cell.

Furthermore, the recent automobile uses a gas-concentration measuring apparatus adapted to automatically diagnose, and inform the driver of, an abnormality of a sensor and sensor controller during combustion control of the engine using a gas sensor as in the foregoing (so-called on-board self-diagnosis).

In those gas-concentration measuring apparatuses, it is a practice to keep and activate the cell (state that temperature is raised to an extent that oxygen ions are fully conductive through the solid electrolyte) at a predetermined temperature (approximately 800° C.) by providing a heater on the cell, in order to make operative the gas sensor cells regardless of exhaust gas temperature. As a method for diagnosing an abnormality of such a gas-concentration measuring apparatus, there is known an abnormality diagnosing method that is to diagnose a short or disconnection abnormality in the state the cell is activated (see JP-A-11-107830).

In the meanwhile, in the foregoing abnormality diagnosing method, abnormality diagnosis is in a state the cell is kept at a predetermined temperature by the heater (in other words, in a cell-activated state). Thus, there is a problem that, where abnormality diagnosis is made based on the voltage across the cell at a relevant time by passing an abnormality-diagnosing current to the cell, there are possible cases a voltage, required for abnormality diagnosis, is not to be outputted onto the respective ends of the cell.

Namely, in the cell-activated state, the cell has an internal resistance of nearly zero. For example, in the event one of the cell electrodes is shorted to the ground (also referred to as GND), the potential difference across the cell becomes nearly zero. This results in a problem that it could not be known which one of the cell electrodes is shorted to GND.

In order to avoid the problem, it can be considered to increase the abnormality-diagnosing current flowing through the cell in the cell-activated state. This however necessitates a current source having a great capacity, which incurs cost increase. Meanwhile, there is another problem that flowing a large current through the cell results in an accelerated deterioration of the cell.

SUMMARY OF THE INVENTION

The present invention has been made in view of such problems, and it is an object thereof to enable an abnormality diagnosis without damaging a gas sensor in the event an abnormality occurs in a gas-concentration measuring apparatus.

A first aspect of the invention made to solve the problem is a method for diagnosing an abnormality of a gas-concentration measuring apparatus, the gas-concentration measuring apparatus comprising: a gas sensor comprising a sensor device for outputting a signal commensurate with a concentration of a predetermined gas in a sample gas space, the sensor device comprising a solid electrolyte and a pair of electrodes provided on the solid electrolyte, and a heating section for heating the sensor device up to an activation temperature at which to output a signal commensurate with a concentration of the predetermined gas, the heating section being externally supplied with power; and a measuring section for measuring a concentration of the predetermined gas in the sample gas space based on an output signal of the sensor device, the measuring section being electrically connected to the electrodes of the sensor device of the gas sensor, the method comprising: restraining a delivery of power to the heating section when a voltage, on any of connection points of between the measuring section and the sensor device of the gas sensor, becomes a preset abnormal voltage value in a state the sensor device is heated to the activation temperature; and thereafter, diagnosing an abnormality of the gas sensor.

According to this, in the event that an abnormality, such as a short circuit, occurs in the gas-concentration measuring apparatus, the temperature of the heating section is lowered by restraining the delivery of power to the heating section. This lowers the temperature of the sensor device to a below of an activation temperature. Because this results in an increased internal resistance of the sensor device, it is possible to positively grasp an abnormality by conducting an abnormality diagnosis in such a high internal resistance state of the sensor device.

Accordingly, in the case that an abnormality-diagnosing current is passed to the sensor device to thereby diagnosing an abnormality based on a voltage across the sensor device at that time for example, a potential difference is provided great across the sensor device because current supply is made in a high internal resistance state of the sensor device, thus enabling a positive abnormality diagnosis.

Here, the activation temperature signifies a temperature in a state that ions such as oxygen ions are allowed to fully conduct in a solid electrolyte.

In the meanwhile, there are cases to use a sensor device structured with a plurality of cells having a solid electrolyte and a pair of electrodes provided thereon, gas a sensor device for a gas sensor of a as-concentration measuring apparatus. The method for diagnosing an abnormality, by means of a gas-concentration measuring apparatus using such a sensor device structured with a plurality of cells, is preferably performed in a second aspect of the invention.

Namely, in the gas-concentration measuring apparatus, the sensor device preferably comprises: a measurement chamber communicating with the sample gas space through a diffusion resistance member; and a plurality of cells each arranged facing the measuring chamber and having a solid electrolyte and a pair of electrodes provided on the solid electrolyte, the measuring section is structured so as to be electrically connected to the plurality of cells of the sensor device and measure a concentration of the predetermined gas in the sample gas space based on an output signal of the plurality of cells, wherein, when a voltage, on any of the connection points of between the measuring section and the plurality of cells of the gas sensor, becomes a preset abnormal voltage value, a delivery of power to the heating section is restrained.

In also a gas-concentration measuring apparatus having, as a gas sensor, a sensor device structured with a plurality of cells (e.g. a full-range air/fuel ratio sensor having two cells or a NOx sensor having three cells) like the above, in the event that an abnormality such as a short circuit occurs, restraining a delivery of power to the heating section lowers the temperature of the heating section. This also lowers the temperature of the cells to a below of the activation temperature. Because this increases the internal resistance of the cell, it is possible to positively grasp an abnormality by conducting an abnormality diagnosis in a high internal resistance state of the cell.

The abnormality diagnosis, of a gas-concentration measuring apparatus using such a gas sensor, is preferably conducted by supplying a predetermined current to the sensor device through the connection points and comparing between detection voltages on the connection points detected during supplying the current in accordance with a third aspect of the invention.

This can positively determine a content and location of an abnormality occurred.

Meanwhile, when conducting abnormality diagnosis, the current to be passed to the sensor device can be reduced to a minimal in magnitude as required for abnormality diagnosis. Thus, abnormality diagnosis is possible to perform without damaging the sensor device.

In the meanwhile, in order to lower the temperature of the sensor device to a below of the activation temperature by restraining the delivery of power, the delivery of power to the heating section is preferably shut off for a predetermined time in accordance with a fourth aspect of the invention.

This can lower the temperature of the sensor device by the simple way of shutting off the delivery of power to the heating section.

Next, a fifth aspect of the invention made to achieve the foregoing object, is an apparatus for diagnosing an abnormality of a gas-concentration measuring apparatus, the gas-concentration measuring apparatus comprising: a gas sensor comprising a sensor device for outputting a signal commensurate with a concentration of a predetermined gas in a sample gas space, the sensor device comprising a solid electrolyte and a pair of electrodes provided on the solid electrolyte, and a heating section for heating the sensor device up to an activation temperature at which to output a signal commensurate with a concentration of the predetermined gas, the heating section being externally supplied with power; and a measuring section for measuring a concentration of the predetermined gas in the sample gas space based on an output signal of the sensor device, the measuring section being electrically connected to the electrodes of the sensor device of the gas sensor, the apparatus for diagnosing an abnormality of a gas-concentration measuring apparatus comprising: a determining section for determining whether or not voltages, on connection points between the measuring section and the sensor device, are a preset abnormal voltage value; a power-delivery control section for restraining a delivery of power to the heating section when a voltage, on any of the connection points, is determined as an abnormal voltage value by the determining section; and an abnormality diagnosing section for diagnosing an abnormality of the gas sensor after restraining a delivery of power by the power-delivery control section.

According to this, as mentioned before, in the event that an abnormality such as a short circuit occurs in the gas-concentration measuring apparatus, the delivery of power to the heating section is restrained, to lower the temperature of the sensor device to a below of the activation temperature and increase the internal resistance of the sensor device. Accordingly, abnormality diagnosis can be positively made according to the abnormality diagnosing method as set forth in the first aspect of the invention.

In the meanwhile, the gas-concentration measuring apparatus includes those using a gas sensor having a sensor device structured with a plurality of cells, as stated before. The gas-concentration measuring apparatus, using a sensor device structured with a plurality of cells, is preferably structured as set forth in a sixth aspect of the invention.

Namely, in the gas-concentration measuring apparatus, the sensor device comprises: a measurement chamber communicating with the sample gas space through a diffusion resistance member; and a plurality of cells each arranged facing the measuring chamber and having a solid electrolyte and a pair of electrodes provided on the solid electrolyte, the measuring section is structured so as to be electrically connected to the plurality of cells of the sensor device and measure a concentration of the predetermined gas in the sample gas space based on an output signal of the plurality of cells, the determining section determines whether or not voltages, on connection points between the measuring section and the plurality of cells of the sensor device, are a preset abnormal value, and the power-delivery control section restrains a delivery of power to the heating section when a voltage, on any of the connection points, is determined as an abnormal voltage value by the determining section.

By structuring a gas-concentration measuring apparatus in this manner, abnormality diagnosis can be positively made according to the abnormality diagnosing method as set forth in the second aspect of the invention.

The abnormality diagnosing section, for a gas-concentration measuring apparatus using such a gas sensor, preferably comprises, as set forth in a seventh aspect of the invention, comprises a current supply section for supplying a predetermined current to the sensor device through the connection points; and a voltage detecting section for detecting voltages on the connection points during supplying a current by the current supply section, wherein the abnormality diagnosing section diagnoses an abnormality by comparing between detection voltages on the connection points detected by the voltage detecting section.

This can positively determine a content and location of an abnormality occurred.

Meanwhile, when conducting abnormality diagnosis, the current to be passed to the sensor device can be reduced to a minimal magnitude as required for abnormality diagnosis. Thus, abnormality diagnosis is possible to perform without damaging the sensor device.

In the meanwhile, in order to lower the temperature of the sensor device to a below of the activation temperature, the delivery of power to the heating section is preferably shut off for a predetermined time by means of the power-delivery control section, as set forth in an eight aspect of the invention.

This can lower the temperature of the sensor device by the simple way of shutting off the delivery of power to the heating section.

BRIEF DESCRIPTION OF THE DRAWINGS

FIG. 3 is a figure showing switch states in various operation modes of the sensor drive circuit 52;

FIG. 4 is a figure showing identifying conditions for identifying an abnormal mode occurring at the terminal;

DETAILED DESCRIPTION OF THE INVENTION

Now, an embodiment of the present invention will be explained on the basis of the drawings.

Figure 1:
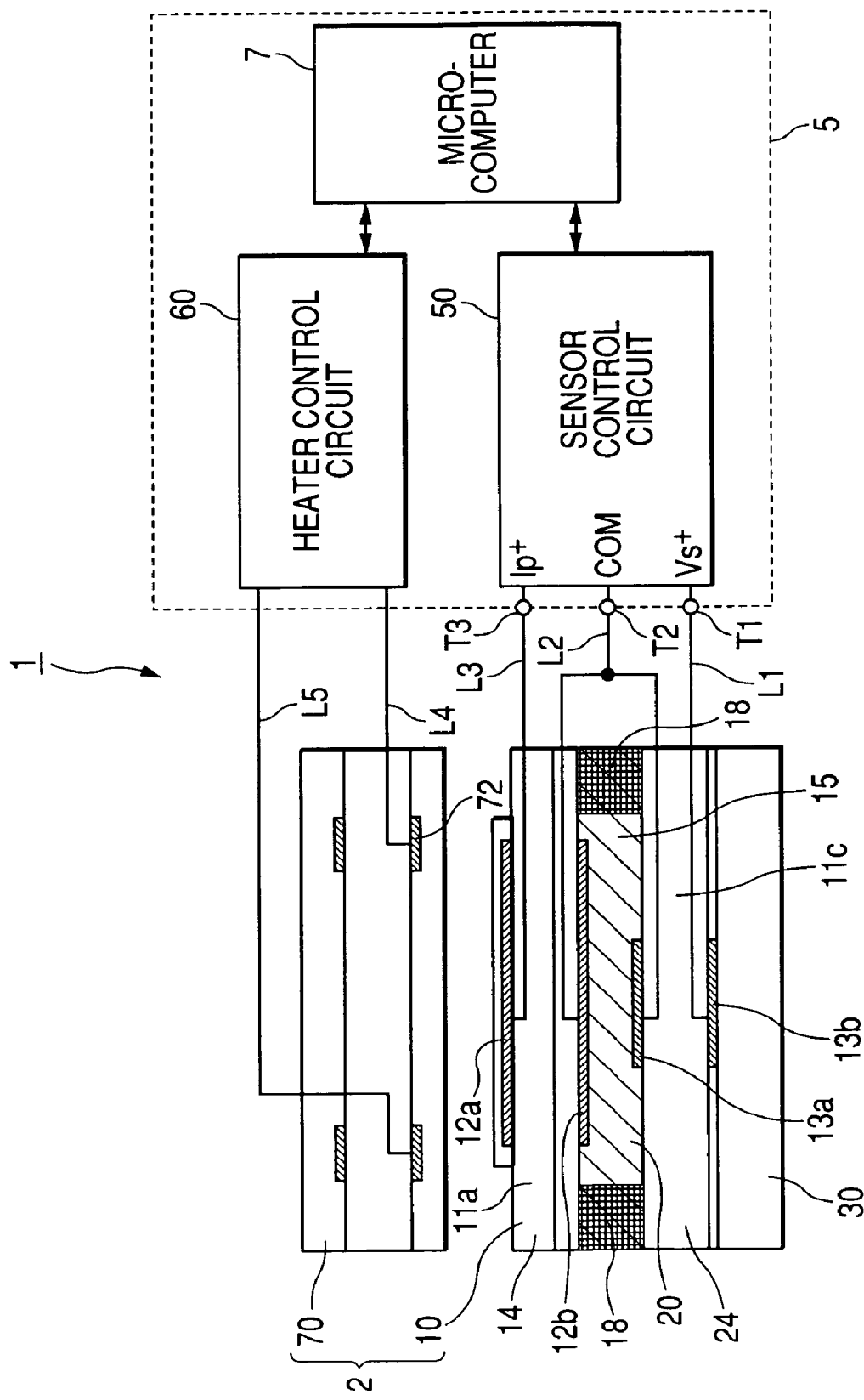
FIG. 1 is a structural view of a gas-concentration measuring apparatus.

FIG. 1 is a schematic diagram showing a structure of a gas-concentration measuring apparatus 1 to which the invention is applied. The gas-concentration measuring apparatus 1 in this embodiment is for measuring a concentration of the oxygen contained in the exhaust gas of an internal combustion engine.

As shown in FIG. 1, the gas-concentration measuring apparatus 1 in this embodiment is constructed with a gas sensor 2, and an electronic control unit 5 (hereinafter, referred also as ECU 5) electrically connected to the gas sensor 2 and having a function to measure, or so, an oxygen concentration of a sample gas.

The gas sensor 2 includes a sensor device 10 that detects an oxygen concentration of a sample gas in the exhaust gas and a heater 70 that keeps the sensor device 10 at an operating temperature.

The sensor device 10 is a full-range air/fuel ratio sensor structured with a pump cell 14, an insulation layer 15, an oxygen-concentration sensing cell 24 and a reinforcing plate 30 that are laid one over another in this order.

The pump cell 14 is made up by a first pump electrode 12a and a second pump electrode 12b that are in a pair arranged on the main and back surfaces of an oxygen-ion conductive solid electrolyte 11a in a sheet form. Of these, the first pump electrode 12a is electrically connected with one end of a line L3. Meanwhile, the second pump electrode 12b is electrically connected with one end of a line L2. The lines L3, L2 have the other ends electrically connected respectively to third and second connection terminals T3, T2 of the ECU 5.

The oxygen-concentration sensing cell 24 is made up by a first sensing electrode 13a and a second sensing electrode 13b that are in a pair arranged on the main and back surfaces of an oxygen-ion conductive solid electrolyte 11c in a sheet form, similarly to the pump cell 14. Of these, the first sensing electrode 13a is electrically connected to the second pump electrode 12b. Consequently, the second pump electrode 12b and the first sensing electrode 13a are connected to the one end of the line L2. Meanwhile, a line L1 at its one end is connected to the second sensing electrode 13b. The other end of the line L1 is electrically connected to a first connection terminal T1 of the ECU 5.

Here, the electrolyte 11a, 11c are formed of a material based on zirconia. The pump electrodes 12a, 12b and sensing electrodes 13a, 13b are formed porous of a material based on platinum.

The insulation layer 15 is laid between the pump cell 14 and the oxygen-concentration sensing cell 24 in order to electrically insulate between the pump cell 14 and the oxygen-concentration sensing cell 24. The insulation layer 15 is formed of a material based on alumina.

Between the pump cell 14 and the oxygen-concentration sensing cell 24, a measurement chamber 20 is formed surrounded by the insulation layer 15. The second pump electrode 12b of the pump cell 14 and the first sensing electrode 13a of the oxygen-concentration sensing cell 24 are arranged facing in the measurement chamber 20. The insulation layer 15, in a part, is formed with a porous diffusion layer 18 communicating with a sample gas side and with a measurement chamber 20, in order to introduce a sample gas of exhaust gas into the measurement chamber 20. The porous diffusion layer 18 is for diffusion control of a sample gas to be introduced into the measurement chamber 20, which is formed porous of a material based on alumina.

The reinforcing plate 30 is arranged on a surface of the oxygen-concentration sensing cell 24 opposite to the measurement chamber 20 so as to place the second sensing electrode 13b therebetween. This secures the strength of the sensor device 10 in the entirety.

Meanwhile, the reinforcing plate 30 shields the second sensing electrode 13b of the oxygen-concentration sensing cell 24 from the outside, to form an enclosure space around the second sensing electrode 13b. In such a device structure, by flowing a slight current Icp in a direction of from the second sensing electrode 13b to first sensing electrode 13a of the oxygen-concentration sensing cell 24, oxygen is pumped toward the second sensing electrode 13b. This accumulates the oxygen nearly constant concentration in the closed space around the second sensing electrode 13b. The oxygen, accumulated in the closed space around the second sensing electrode 13b, serves as a reference oxygen for detecting an oxygen concentration of a sample gas in the sensor device 10. For this reason, the second sensing electrode 13b is also termed a self-generating reference electrode 13b.

Incidentally, the reinforcing plate 30 is nearly equal in size to the solid electrolyte 11a, 11c constituting the pump cell 14 and oxygen-concentration sensing cell 24, and formed in a plate form of a material based on ceramic.

The heater 70 is formed flat and arranged opposed to the pump cell 14 of the sensor device 10. The heater 70, formed of a material based on alumina, has therein a heater wire 72 formed of a material based on platinum. The heater 70 is controlled according to a power supplied from a heater control circuit 60, referred later, such that the temperature of the sensor device 10 becomes 550-900° C. The heater wire 72 has respective ends electrically connected with one ends of lines L4, L5. The lines L4, L5 respectively have the other ends electrically connected to the heater control circuit 60 of the ECU 5. Note that the heater 70 corresponds to heating section as set forth in the claims.

By keeping the cells at 550-900° C. by means of the heater 70, the solid electrolytic layer of the cell is placed in a state fully conductive of oxygen ions, so-called an activated state. Due to this, the pump cell 14 is allowed for pumping of oxygen ions and the oxygen-concentration sensing cell 24 to generate a voltage commensurate with the difference in oxygen concentration between the measurement chamber 20 and the self-generating reference electrode 13b.

The electronic control unit 5 includes a sensor control circuit 50 electrically connected to the sensor device 10 and for taking control of the sensor device 10, a heater control circuit 60 electrically connected to the heater 70 and for taking control of the heater 70, and a microcomputer 7 for taking control of the sensor control circuit 50 and the heater control circuit 60.

Of these, the microcomputer 7 includes, though not shown, a CPU as a central processing unit, a RAM and ROM storing data and programs, etc., and input and output ports for signal input/output from/to an external circuit. The microcomputer 7 is controlled to execute instructions, such as of operation or data transfer, according to a program stored in the RAM, etc. In the microcomputer 7, the signal inputted to its input port is reflected in the content of an input-port register while the content stored in the output-register is outputted as a signal onto its output port.

The sensor control circuit 50 has terminals Vs+, COM and Ip+. These terminals are electrically connected to the first to third connection terminals T1-T3 of the ECU 5. Accordingly, the second sensing electrode 13b of the sensor device 10 is electrically connected to the terminal Vs+ through the line L1 and first connection terminal T1. The second pump electrode 12b and first sensing electrode 13a of the sensor device 10 is electrically connected to the terminal COM through the line L2 and second connection terminal T2. Furthermore, the first pump electrode 12a of the sensor device 10 is electrically connected to the terminal Ip+ through the line L3 and third connection terminal T3.

In the sensor device 10, the oxygen in a sample gas diffuses into the measurement chamber 20 through the porous diffusion layer 18, commensurate with the oxygen concentration of the sample gas. In a state the air-fuel mixture to be delivered to the engine is kept at a stoichiometric ratio, the sensor device 10 has a characteristic to generate an electromotive force 450 mV at the oxygen-concentration sensing cell 24 due to the difference of oxygen concentration between the measurement chamber 20 and the closed space, providing a reference of oxygen concentration, around the second sensing electrode 13b. Namely, a potential difference 450 mV takes place at between the first and second sensing electrodes 13a, 13b.

In the meanwhile, the oxygen contained in the exhaust gas has a concentration changing with a change in air/fuel ratio of the mixture to be delivered to the engine. This causes a change in the concentration of the oxygen contained in the atmosphere of within the measurement chamber 20 of the sensor device 10. Therefore, in the gas-concentration measuring apparatus 1 of this embodiment, the current Ip through the pump cell 14 is placed under control of the sensor control circuit 50, referred later, to provide a potential difference 450 mV to between the first and second sensing electrodes 13a, 13b. Namely, oxygen pumping is made by the pump cell 14 such that the atmosphere in the measurement chamber 20 becomes equal to a stoichiometric air/fuel ratio. Depending upon the current Ip, measurement is made as to an oxygen concentration of the sample gas.

Figure 2:
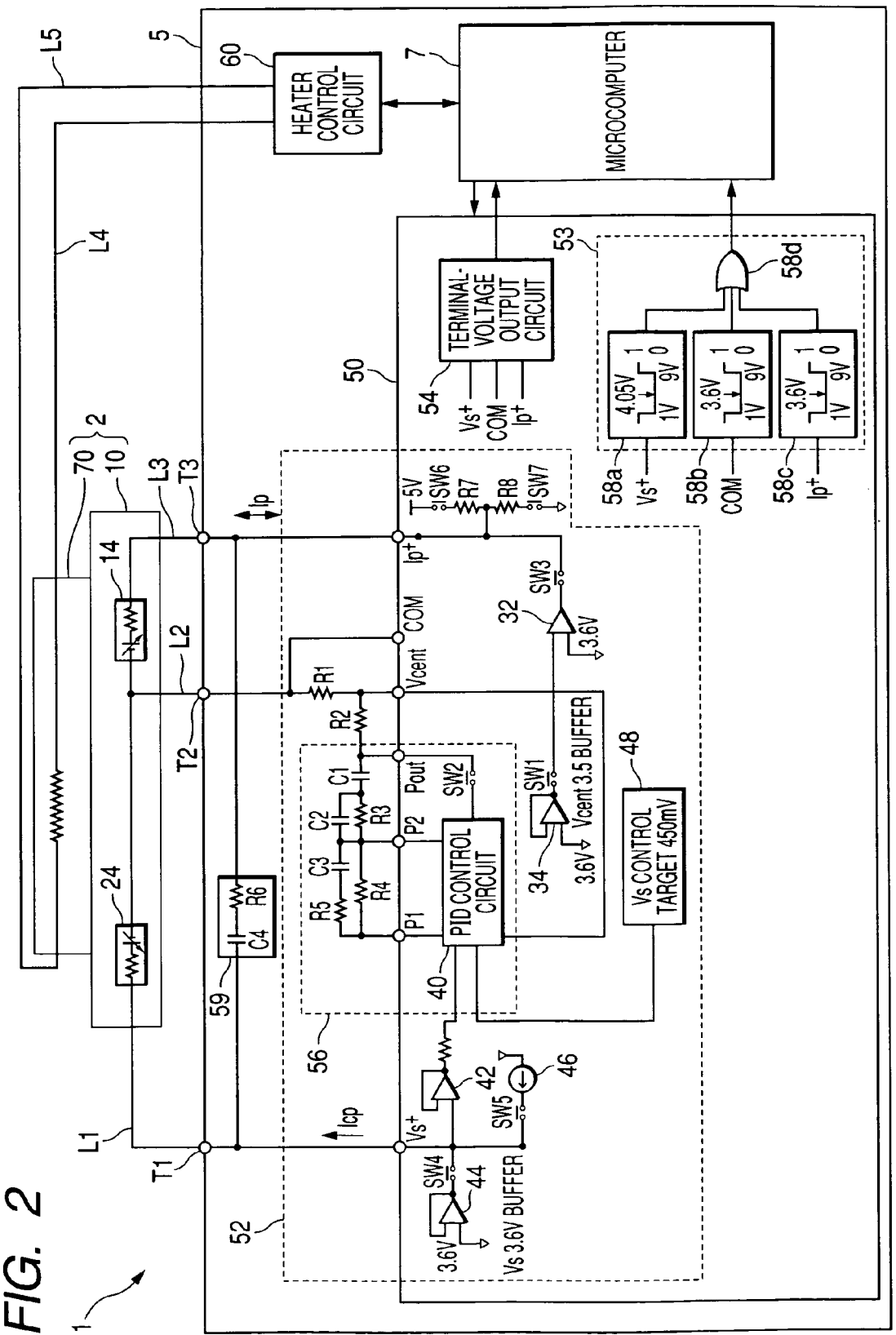
FIG. 2 is a circuit diagram showing the outline of an electronic control unit 5.

Based on FIG. 2, explanation is now made on the configuration and operation of the ECU 5. FIG. 2 is a circuit diagram showing the outline of the ECU 5.

As shown in FIG. 2, the ECU 5 includes a sensor control circuit 50 for taking control of sensor device 10, a heater control circuit 60 for taking energization-control of the heater and a microcomputer 7 for taking control of the sensor control circuit 50 and heater control circuit 60.

The sensor control circuit 50 includes a sensor drive circuit 52 for drive-controlling the pump cell 14 and oxygen-concentration sensing cell 24 constituting the sensor device 10, an abnormality detecting circuit 53 for outputting, to the microcomputer 7, an abnormality-detection flag DIAG=1 that is provided when any of respective terminal voltages on the terminals Vs+, COM and Ip+, as connection points between the sensor device 10 and the sensor drive circuit 52, become out of a predetermined voltage range, and a terminal-voltage output circuit 54 for outputting the terminal voltages on the terminals Vs+, COM and Ip+ to the microcomputer 7. The sensor control circuit 50 is realized by an ASIC (Appliance Specific IC), for example.

The sensor drive circuit 52 includes an operational amplifier 32 for flowing a current Ip to drive the pump cell 14, a PID control circuit 56 for controlling the voltage of the oxygen-concentration sensing cell 24 to a target control voltage (e.g. 450 mV), a constant current source 46 for flowing a constant current Icp to the oxygen-concentration sensing cell 24 in order to keep constant the oxygen concentration at the selg-generated-reference electrode 13b, a constant voltage source 48 for supplying a control-target voltage of current Ip, terminals Vs+, COM and Ip+ for connecting between the sensor drive circuit 52 and the sensor device 10, terminals P1, P2 and Pout for use in separately providing devices that determine a control characteristic of PID control circuit 56, and switches SW1-SW7 for changing the operation mode of the sensor drive circuit 52 depending upon an operation-mode-switch signal outputted from the microcomputer 7. Note that the terminals Vs+, COM and Ip+ are respectively connected to the first to third connection terminals T1, T2, T3.

The first pump electrode 12a, of the electrodes in one pair constituting the pump cell 14, is connected to the terminal Ip+ through the line L3 and third connection terminal T3. The second pump electrode 12b is connected, through the line L2 and second connection terminal T2, to the terminal COM that provides a common reference voltage to the sensor device 10. The second pump electrode 12b is connected, besides to the terminal COM, to a terminal Vcent through the line L2, second connection terminal T2 and resistance R1. The second sensing electrode 13b, of the sensing electrodes in one pair constituting the oxygen-concentration sensing cell 24, is connected to the terminal Vs+ through the line L1 and first connection terminal T1 while the first sensing electrode 13a is to the terminal COM through the line L2 and second-connecting terminal T2.

To the terminal Ip+ are connected a resistance R7, a resistance R8 and an operational amplifier 32. Of these, the resistance R7, at its one end, is connected to the terminal Ip+ while the resistance R7, at its other end, is connected to a power source 5V through a switch SW6. The resistance R8, at its one end, is connected to the terminal Ip+ while the resistance R8, at its other end, is grounded through a switch SW7. Here, the resistance values of the resistances R7, R8 are preferably about 50 kΩ to prevent a leak current from flowing when the operation mode of the sensor drive circuit 52 is a gas-concentration measurement mode described later. The operational amplifier 32 has an inverted input terminal to which the PID control circuit 56 is connected through a resistance R2, a non-inverted input terminal to which a reference voltage 3.6 V is applied, and an output terminal connected to the terminal Ip+ through a switch SW3. Those constitute a negative feedback circuit taking control of the sensor device 10.

The PID control circuit 56 and the operational amplifiers 32, 34 are connected to the terminal COM. Of these, the PID control circuit 56 has a function to PID-operate a deviation ΔVs of the output voltage from the oxygen-concentration sensing cell 24 relative to the control-target voltage 450 mV, and control it toward the control-target voltage (e.g. 450 mV). The PID control circuit 56 is configured with a PID control circuit 40, and resistances R3-R5 and capacitors C1-C3 that are fit to the terminals P1 and P2 and to determine a control characteristic of the PID control circuit 56. The PID control circuit 56 is connected to the terminal Vs+ through the operational amplifier 42, to input an output voltage Vs of the oxygen-concentration sensing cell 24 to the PID control circuit 56. The PID control circuit 56 is connected to the terminal Pout through the switch SW2. The terminal Pout is connected to the terminal Vcent through the resistance R2 and, finally, to the non-inverted input terminal of the operational amplifier 32. The PID control circuit 56 is connected to the terminal COM through the switch SW2 and resistances R1, R2. Note that the output of the PID control circuit 56 is to be controlled on-off by the switch SW2.

The constant-voltage source 48 is connected to the PID control circuit 40. The constant-voltage source 48 is a circuit, for supplying a control-target voltage 450 mV to control the current Ip, to the PID control circuit 56.

The operational amplifier 32, at its non-inverted input terminal, is connected to the terminal COM through the resistance R1.

The operational amplifier 34 is connected to the terminal Vcent through the switch SW1. The operational amplifier 34 is a circuit that supplies an abnormality-identifying current in order to diagnose an abnormality of the sensor device 10 as referred later.

The constant-voltage source 46 and the operational amplifiers 42, 44 are connected to the terminal Vs+. Of these, the constant-current source 46 is connected to the terminal Vs+ through the switch SW5. The constant-current source 46 is a circuit that supplies a constant current Icp (e.g. 17 μA) to flow to the oxygen-concentration sensing cell 24, in order to keep the oxygen concentration constant at around the self-generated-reference electrode 13b of the oxygen-concentration sensing cell 24. The operational amplifier 44 is connected to the terminal Vs+ through the switch SW4. This operational amplifier 44 is a circuit that supplies an abnormality-identifying current in order to diagnose an abnormality of the sensor device 10 as referred later, similarly to the operational amplifier 34. The operational amplifier 42 has a non-inverted input terminal connected to the terminal Vs+.

Incidentally, between the terminal Vs+ and the terminal Ip+, inserted is an oscillation-preventing circuit 59 formed by a series circuit of resistance R6 and capacitor C4, in order to prevent the sensor drive circuit 52 from oscillating.

In the sensor drive circuit 52 thus configured, the switches SW2, SW3, SW5, SW6 and SW7 are turned on and the switches SW1 and SW4 are turned off, in order to measure an oxygen concentration of a sample gas. In the case the sample gas at this time is in a state of excessive supply of fuel (rich), the oxygen in the measurement chamber 20 is deficient in concentration relative to the stoichiometric air/fuel ratio, the oxygen-concentration sensing cell 24 has an output voltage Vs higher than the control-target voltage 450 mV. This accordingly causes a deviation ΔVs in the output voltage Vs relative to the control-target voltage. The deviation ΔVs is PID-operated by the PID control circuit 56 and fed back by the operational amplifier 32. Consequently, a current Ip is caused to flow to the pump cell 14, in order to pump an insufficient amount of oxygen into the measurement chamber 20 by means of the pump call 14.

Meanwhile, in the case the sample gas is in a status of insufficient supply of fuel (lean), the oxygen in the measurement chamber 20 is excessive in concentration relative to the stoichiometric air/fuel ratio, the oxygen-concentration sensing cell 24 has an output voltage Vs lower than the control-target voltage 450 mV. Thus, the operational amplifier 32 feed back a deviation ΔVs similarly to the above. This causes a current Ip to flow through the pump cell 14, in order to pump an excessive amount of oxygen out of the measurement chamber 20 by means of the pump call 14.

In this manner, in the gas-concentration measuring apparatus 1 of this embodiment, the current Ip for pump cell 14 control is measured such that the output voltage Vs of the oxygen-concentration sensing cell 24 becomes 450 mV, thus enabling to measure an oxygen concentration of a sample gas. Note that the gas-concentration measuring apparatus 1 of this embodiment is configured to voltage-convert the current Ip flowing through the pump cell 14 by the resistance R2, and to output a voltage across the resistance R2 (specifically, a voltage of between the terminals Vcent and Pout) to an input port of the microcomputer 7 through a differential amplifier circuit, not shown. Engine combustion control is finally effected depending upon an oxygen concentration measured at the microcomputer 7.

Next, the abnormality detecting circuit 53 is configured with window comparators 58a, 58b, 58c and an OR circuit 58d. The comparators 58a, 58b, 58c has respective output terminals parallel connected to an input terminal of the OR circuit 58d. Although omitted of connection lines in the figure, the comparators have input terminals respectively connected to the terminals Vs+, COM and Ip+.

The window comparator 58a, 58b, 58c is configured to output a low-level signal when the terminal voltage on the terminal Vs+, COM, Ip+ is in a predetermined voltage range, and a high-level signal when the terminal voltage on the terminal is out of the predetermined voltage range.

The terminal-Vs+ voltage is usually kept at 4.05 V that is a value the reference voltage 3.6 V on the terminal COM is added with an output voltage Vs (450 mV) of the oxygen-concentration sensing cell 24. However, in the event that the line L1 or the like connected to the terminal Vs+ (also referred to as line Vs+) is shorted to the power-source potential or the ground potential due to a certain cause, the terminal-Vs+ voltage changes into the power-source or ground potential. Thereupon, an excessive abnormal current flows through the sensor device 10, which possibly damages the sensor device 10. For this reason, the window comparator 58a is configured to compare the terminal-Vs+ voltage with a preset threshold, to output a high level signal when the terminal-Vs+ voltage exceeds the threshold. Specifically, the threshold at the window comparator 58a has an upper limit set at 9 V or at a predetermined voltage value subtracted a predetermined value (e.g. 1.5 V) from the power-source voltage in consideration of the variation in power-source voltage to the sensor control circuit 50. Simultaneously, the lower limit of the threshold is set at 1 V that a ground float is considered for the ground level 0 V. Thus configuration is provided such that, when the terminal-Vs+ voltage rises above the upper limit 9 V or the predetermined voltage or when the terminal-Vs+ voltage drops below the lower limit 1 V, the window comparator 58a outputs a high level signal.

The terminal-COM voltage is usually controlled at a reference voltage 3.6 V by means of the operational amplifier 32. However, in the event that the line L2 or the like connected to the terminal COM (also referred to as line COM) is shorted to the power-source potential or the ground potential due to a certain cause, the terminal-COM voltage changes into the power-source or ground potential. For this reason, the window comparator 58b is configured to compare the terminal-COM voltage with a preset threshold, to output a high level signal when the terminal-COM voltage exceeds the threshold. Specifically, the threshold at the window comparator 58b has an upper limit set at 9 V or at a predetermined voltage value, similarly to the window comparator 58a. Simultaneously, the lower limit of the threshold is set at 1 V. Thus, configuration is made such that, when the terminal-COM voltage rises above the upper limit 9 V or the predetermined voltage or when the terminal-COM voltage drops below the lower limit 1 V, the window comparator 58b outputs a high level signal.

At also the terminal Ip+, when the line L3 or the like connected to the terminal Ip+ (also referred to as line Ip+) is shorted to the power-source potential or the ground potential due to a certain cause, the terminal voltage on the terminal Ip+ changes into the power-source or ground potential. For this reason, the window comparator 58c is configured to compare the terminal-Ip+ voltage with a preset threshold, to output a high level signal when the terminal-Ip+ voltage exceeds the threshold. Specifically, for also the window comparator 58c to which a terminal-Ip+ voltage is to be inputted, its upper limit value is set at 9 V or at a predetermined voltage value and its lower limit value is set at 1V, in a manner sandwiching the reference voltage 3.6 V, similarly to the window comparator 58b. Thus configuration is provided such that, when the terminal-Ip+ voltage rises above the upper limit 9 V or the predetermined voltage value or when the terminal-Ip+ voltage drops below the lower limit 1 V, the window comparator 58c outputs a high level signal.

The OR circuit 58d calculates a logical sum of the signals of from the window comparators 58a, 58b, 58c. When there is an input of a high level signal from any of the window comparators 58a, 58b, 58c, an abnormality detection flag DIAG is rendered as DIAG=1 and outputted to the microcomputer 7. When the terminal voltages at the terminals Vs+, COM and Ip+ are each within a predetermined voltage range, the abnormality detecting circuit 53 renders the abnormality detection flag DIAG as DIAG=0 and outputs it to the microcomputer 7. In thus manner, the abnormality detecting circuit 53 has a function to render the abnormality detecting flag DIAG as DIAG=1 in the event a short abnormality occurs on any of the lines Vs+, COM and Ip+ and the terminal voltage at the terminal Vs+, COM or Ip+ exceeds the threshold into an abnormal voltage value (in other words, when abnormality occurs in the sensor device 10). Note that the window comparators 58a, 58b, 58c correspond to a determining section set forth in the claims.

The terminal-voltage output circuit 54 is a circuit for outputting a terminal voltage of the terminal Vs+, COM and Ip+ to the microcomputer 7 when the operation mode of the sensor drive circuit 52 is an abnormality diagnostic mode described later. Note that, although connection lines are omitted in the figure, the terminal-voltage output circuit 54 at its input terminals is respectively connected to the terminals Vs+, COM and Ip+.

The microcomputer 7 is connected to the sensor drive circuit 52, the abnormality detecting circuit 53 and the terminal-voltage output circuit 54. Specifically, the switch signal, referred later, for changing over the operation mode of the sensor drive circuit 52 (specifically, control signal for controlling on-off of the switches SW1-SW7) is connected to an output port of the microcomputer 7 while the abnormality detecting flag DIAG of the abnormality detecting circuit 53, the output signal of the terminal-voltage output circuit 54 and the signal of voltage across the resistance R2 are connected to the input ports of the microcomputer 7. Consequently, the microcomputer 7 is allowed to take control of operation mode as to the sensor drive circuit 52, and to obtain information about the presence/absence of an abnormality continuing on the sensor device 10, terminal voltages at the terminals and an oxygen-concentration measurement of the sample gas. Meanwhile, the microcomputer 7 makes an abnormality diagnosis of the sensor device 10 depending upon an input signal from the abnormality detecting circuit 53 and terminal-voltage output circuit 54. Note that the microcomputer 7 corresponds to a voltage-detecting section and an abnormality diagnosing section as set forth in the claims.

The heater control circuit 60 has a heater-energizing switch, not shown. The heater circuit 60 controls on-off the heater-energizing switch depending upon a signal from the microcomputer 7, and in turn PWM-controls the power of from the battery, thereby controlling the delivery power to the heater 70. This can keep the temperature of the sensor device 10 at 550-900° C.

Meanwhile, the heater control circuit 60 regulates the on-off duty ratio of the heater-energizing switch into a duty ratio 0%, thereby ceasing the power delivery to the heater 70. Note that the heater control circuit 60 corresponds to a power-delivery control section as set forth in the claims.

In the sensor drive circuit 52 in this embodiment, its operation mode is switched over to a gas-concentration measurement mode, a protection mode or an abnormality diagnostic mode by turning the switches SW1-SW7 to on/off.

The gas-concentration measurement mode is an operation mode for performing combustion control of the engine. In the normal state where there is no abnormality occurring in the sensor device 10, the sensor drive circuit 52 is placed in this operation mode. In this operation mode, the switches SW2, SW3, SW5, SW6, SW7 are on while the switches SW1, SW4 are off in the sensor drive circuit 52, as shown in FIG. 3.

When the switches SW2, SW3, SW5, SW6, SW7 are on and the switches SW1, SW4 are off in this manner, the pump cell 14 is placed under negative-feedback control by the operational amplifier 32, based on the output voltage Vs of the oxygen-concentration sensing cell 24 as a negative feedback voltage. The oxygen concentration of the sample gas can be measured by measuring the current Ip. Thus, engine combustion control is effected based on the oxygen concentration measured.

The protection mode is an operation mode that, when it is detected by the abnormality detecting circuit 53 that the terminal voltage at any of the terminals Vs+, COM and Ip+ is outside the predetermined voltage range, all the output from the sensor drive circuit 52 to the sensor device 10 are turned off (in other words, electrically cut off between the sensor drive circuit 52 and the sensor device 10), thereby protecting the sensor device 10.

In this operation mode, because all the switches SW1-SW7 in the sensor drive circuit 52 are off as shown in FIG. 3, the signals inputted from the operational amplifiers 32, 34, 44, the PID control circuit 40 and the constant-current source 46 are rendered off, to electrically cut off between the sensor device 10 and the sensor drive circuit 52. Accordingly, this eliminate an abnormal current from continuously flowing to the sensor device 10, thus electrically protecting the sensor device 10.

The abnormality diagnostic mode is an operation mode that is to diagnose an abnormal terminal and content of the abnormality when there is an occurrence of abnormality on the sensor device 10 during operation of the vehicle.

In this operation mode, the heater-energizing switch of the heater control circuit 60 is first controlled to a duty ratio 0%, thereby ceasing the power delivery of from the heater control circuit 60 to the heater 70. By ceasing the power delivery to the heater 70, the temperature of the sensor device 10 lowers down to an inactivation temperature (less than 550° C. in this embodiment), thus increasing the internal resistance of the pump cell 14 and oxygen-concentration sensing cell 24.

After ceasing the power delivery to the heater 70, the switches SW1, SW4, SW6, SW7 of the sensor drive circuit 52 turn on and the switches SW2, SW3, SW5 are turned off, as shown in FIG. 3.

In this manner, because the switch SW3 is off, no current is supplied from the operational amplifier 32 driving the pump cell 14. Meanwhile, because the switch SW2 is off, no current is supplied from the PID control circuit 40, thus ceasing the current control for the pump cell 14. Accordingly, the negative feedback control of the pump cell 14 is not performed.

Because the switches SW1, SW4, SW6, SW7 are on, a current is supplied from the operational amplifier 34, 44 to the pump cell 14 and oxygen-concentration sensing cell 24. Note that the operational amplifiers 34, 44 correspond to a current supply section as set forth in the claim.

When the currents output from the operational amplifiers 34, 44 is flowed to the cells 14, 24 (hereinafter, referred to also as abnormality-identifying currents), the respective terminal voltages (referred to also as voltages Vs+, COM and Ip+, respectively) occurred at the respective terminals (terminals Vs+, COM and Ip+) are input from the terminal-voltage output circuit 54 into the microcomputer 7. The microcomputer 7 compares the terminal voltages inputted and identifies which one of the conditions shown in FIG. 4 the terminal voltages are fallen under in state, thus determining a terminal abnormal and a content thereof.

Specifically, in the event that a short occurs to the ground potential (hereinafter, referred to also as a GND short) on any of the lines Vs+, COM and Ip+, when the terminal voltages are in a relationship of voltage Vs+<voltage COM and voltage Vs+<voltage Ip+, then there is a GND short occurring on the line Vs+. When the terminal voltages are in a relationship of voltage Ip+<voltage COM and voltage Ip+<voltage Vs+, then there is a GND short occurring on the line Ip+. In other cases, there is determined a GND short occurring on the line COM.

Likewise, in the event that a short to the power potential (hereinafter, referred to also as a VB short) occurs on any of the lines Vs+, COM and Ip+, when the terminal voltages are in a relationship of voltage Vs+>voltage COM and voltage Vs+>voltage Ip+, then there is a VB short occurring on the line Vs+. When the terminal voltages are in a relationship of voltage Ip+>voltage COM and voltage Ip+>voltage Vs+, then there is a VB short occurring on the line Ip+. In other cases, there is determined a VB short occurring on the line COM.

Here, the abnormality-identifying current outputted from the operation amplifier 34, 37 is assumed 5 mA or greater in consideration of an output voltage of the pump cell 14 and oxygen-concentration sensing cell 24 varying depending upon an oxygen concentration of the sample gas. This current is set such that the terminal voltage appearing on the terminal during supplying an abnormality-identifying current is greater than the voltage to be outputted responsive to an oxygen concentration of the sample gas by the pump cell 14 or oxygen-concentration sensing cell 24. This enables to correctly perform an abnormality diagnosis.

Figure 5:
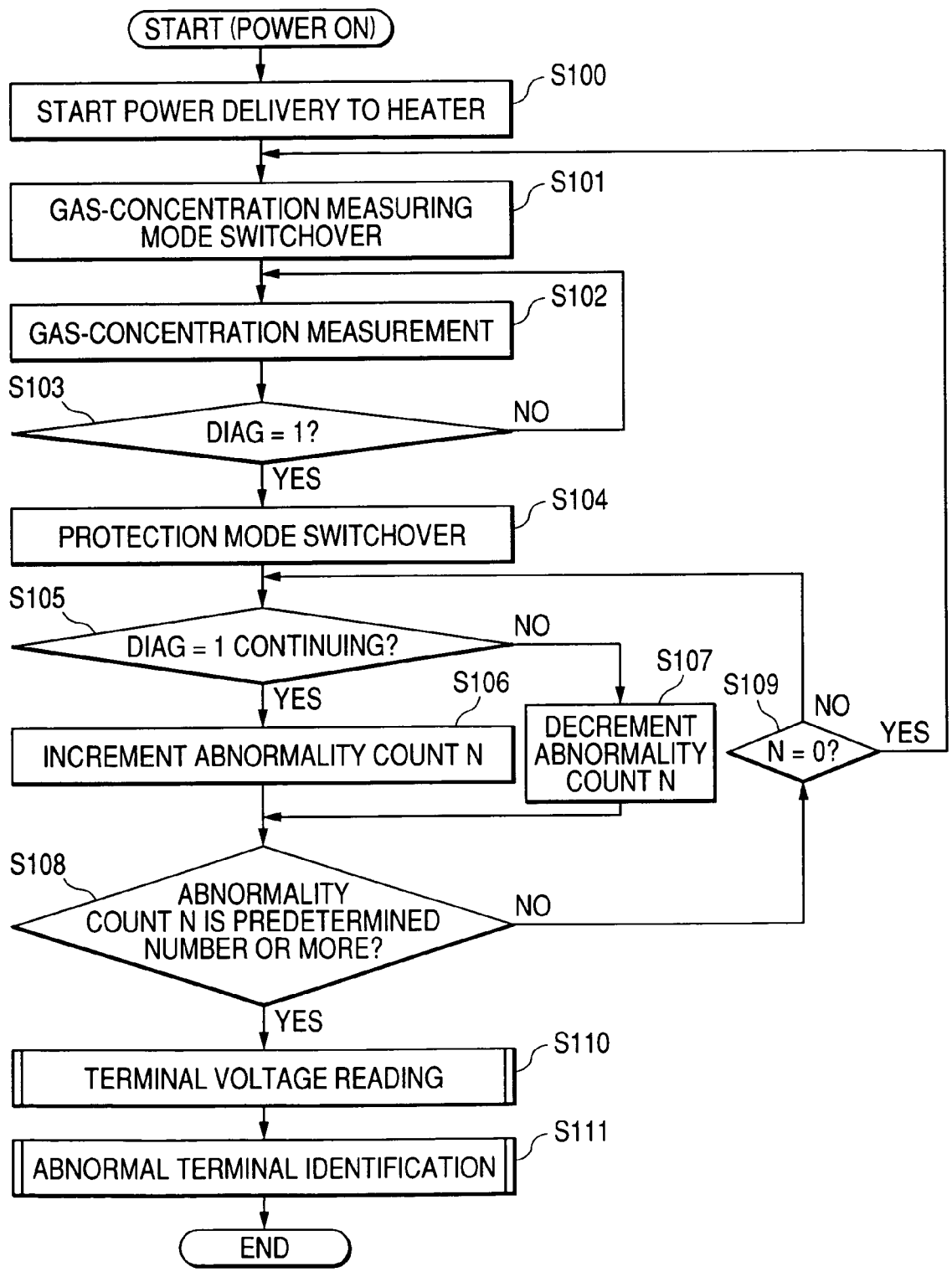
FIG. 5 is a main flowchart showing a flow of process steps to be executed in a microcomputer 7.
Figure 6:
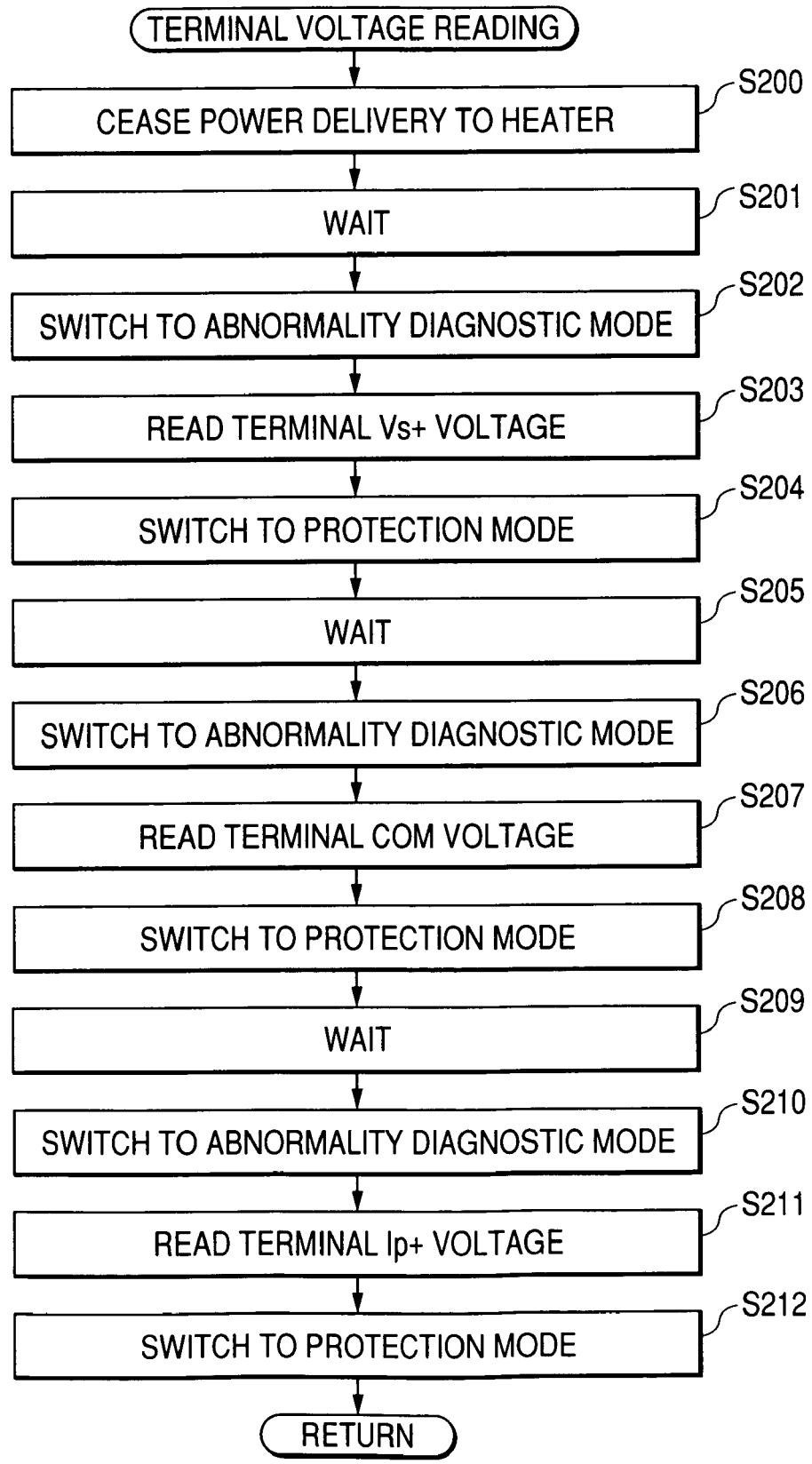
FIG. 6 is a subroutine flowchart showing a flow of process steps to be executed in a microcomputer 7.

Now, explanation is made on a process flow to be executed on the microcomputer 7, according to FIGS. 5 and 6.

FIG. 5 is a main flowchart showing a process flow to be executed on the microcomputer 7 while FIG. 6 is a flowchart of a subroutine invoked from the main flowchart shown in FIG. 5.

As shown in FIG. 5, the microcomputer 7 starts its process upon powering on the automobile, and causes the heater control circuit 60 to deliver power to the heater 70 after internally initializing the microcomputer 7 (S100). After activating the sensor device 10, the microcomputer 7 outputs to the sensor drive circuit 52 a signal for switching the operation mode into a gas-concentration measurement mode (switch-to-gas-concentration-measurement-mode signal) (S101). By inputting the switch-to-gas-concentration-measurement-mode signal to the sensor drive circuit 52, the switches SW2, SW3, SW5, SW6, SW7 thereof are turned on while the switches SW1, SW4 are turned off. This switches the sensor drive circuit 52 in its operation mode into a gas-concentration measurement mode. At step S102, executed is a measuring process as to an oxygen concentration of the sample gas.

At S103, it is determined whether or not the abnormality detection flag DIAG outputted from the abnormality detecting circuit 53 is DIAG=1. If not DIAG=1, i.e. if the terminal voltages of the sensor device 10 are each within a predetermined voltage range (when there is no abnormality occurrence in the sensor device 10), the process returns to S102 where repeatedly executed is a process measuring an oxygen concentration of the sample gas.

Meanwhile, if DIAG=1 at S103, the sensor drive circuit 52 turns off the switches SW1-SW7, to place the sensor drive circuit 52 in its operation mode into a protection mode (S104). This electrically cuts off between the sensor device 10 and the sensor drive circuit 52, to prevent the damage to the sensor device 10 due to flowing of an abnormal current into the sensor device 10.

At S105, it is determined whether or not DIAG=1 is now continuing. If DIAG=1 is continuing, the process proceeds to S106 where abnormality count N is incremented, followed by proceeding of the process to S108. Meanwhile, if DIAG=1 is not continuing, the process proceeds to S107 where abnormality count N is decremented, followed by proceeding of the process to S108.

At S108, it is determined whether or not the abnormality count N is equal to or greater than a predetermined count. If the abnormality count N is equal to or greater than the predetermined count, established is a fact there is an abnormality occurrence in the sensor device 10, and the process proceeds to S110. Meanwhile, if the abnormality count N is not equal to or greater than the predetermined count, the process proceeds to S109.

At S109, it is determined whether or not the abnormality count N is N=0. If the abnormality count N=0, the sensor device 10 is determined eliminated of abnormality, and the process returns to S101. Thereafter, the process proceeds to S102 where repeatedly executed is a process to measure an oxygen concentration of the sample gas. Meanwhile, if the abnormality count is not N=0 at S109, the process of S105-S108 is repeatedly executed.

At S110, terminal-voltage-reading is executed. Referring to FIG. 6, explanation is made on the terminal-voltage-reading. In the terminal-voltage-reading, the heater-energizing switch of the heater control circuit 60 is first controlled to a duty ratio 0%, to cease the power delivery to the heater 70 (S200). Then, using a timer, not shown, haven by the microcomputer 7, the process waits for a predetermined time period (100 ms-1 s, e.g. for 1 s) (S201). The reason of executing the process to wait for the predetermined time period is because of the following reason. Namely, even in case the power delivery to the heater 70 is ceased by controlling the heater-energizing switch of the heater control circuit 60 to a duty ratio 0%, the temperature of the pump cell 14 and oxygen-concentration sensing cell 24 does not immediately lower down to an inactivation temperature. Consequently, a wait process for a predetermined time period is executed until the temperature of the pump cell 14 and oxygen-concentration sensing cell 24 lowers down to an inactivation temperature. Meanwhile, the sensor drive circuit 52 is provided with an oscillation-preventing circuit 59. The terminal voltages at the terminals (Vs+, COM, Ip+) are transiently in an instable state in a predetermined time period after electrically cutting off between the sensor device 10 and the sensor drive circuit 52 by placing the operation mode of the sensor drive circuit 52 in a protection mode. In such an instable state, it is impossible to correctly obtain a voltage on the terminal. For this reason, a wait process for a predetermined time period is executed to wait until the voltage at each terminal becomes stable in state. After waiting for a predetermined time period, the process proceeds to S202.

At S202, a signal for switching the operation mode into abnormality diagnostic mode (switch-to-abnormality-diagnostic-mode signal) is outputted to the sensor drive circuit 52. By inputting of the switch-to-abnormality-diagnostic-mode signal, the sensor drive circuit 52 turns on the switches SW1, SW4, SW6, SW7 and turns off the switches SW2, SW3, SW5. This switches the sensor drive circuit 52 in its operation mode into an abnormality-diagnostic mode.

At S203, read is a terminal voltage to the terminal Vs+ which voltage is outputted from the terminal-voltage output circuit 54. The read terminal voltage Vs+ is stored into a RAM, not shown, of the microcomputer 7.

At S204, outputted is a signal for switching the operation mode into a protection mode (switch-to-protection signal), to the sensor drive circuit 52. By inputting the switch-to-protection signal to the sensor drive circuit 52, the switches SW1-SW7 are turned off. This switches the operation mode of the sensor drive circuit 52 from the operation mode into a protection mode.

At S205, the process waits for a predetermined time period and then proceeds to S206, similarly to S201. At S206, a switch-to-abnormality-diagnostic-mode signal is outputted to the sensor drive circuit 52. By inputting the switch-to-protection-mode signal to the sensor drive circuit 52, the switches SW1, SW4, SW6, SW7 are turned on and the switches SW2, SW3, SW5 are turned off. This switches the operation mode of the sensor drive circuit 52 into an abnormality diagnostic mode.

At S207, read is a terminal voltage COM which voltage is outputted from the terminal-voltage output circuit 54. The read terminal voltage COM is stored in a RAM, not shown, of the microcomputer 7.

At S208, a switch-to-protection-mode signal is outputted to the sensor drive circuit 52. By inputting the switch-to-protection-mode signal to the sensor drive circuit 52, the switches SW1-SW7 are turned off. This switches the operation mode of the sensor drive circuit 52 into a protection mode.

At S209-S212, the process is performed similarly to the above. Namely, by outputting a switch-to-abnormality-diagnostic-mode signal is to the sensor drive circuit 52 at S210 after waiting for a predetermined time period at S209, the operation mode of the sensor drive circuit 52 is switched into an abnormality diagnostic mode. Thereafter, at S211, read is a terminal voltage Ip+. The read terminal voltage Ip+ is stored in the RAM, not shown, of the microcomputer 7. At S212, by outputting a switch-to-protection-mode signal to the sensor drive circuit 52, the operation mode of the sensor drive circuit 52 is switched into a protection mode.

The process then proceeds to an abnormal-terminal-identifying step (S111) of the main flowchart (FIG. 5). At S111, the terminal voltages, stored at S203, S207 and S211 in the RAM of the microcomputer 7, are identified according to the identification condition shown in FIG. 4, to determine a content of and terminal of an abnormality occurred. The identification result is stored in the RAM, not shown, of the microcomputer 7. By the abnormal terminal identification, determination is done as to which one of GND short and VB short the abnormality occurred in the sensor device 10 is and which one of the terminals Vs+, COM and Ip+ the abnormality occurred.

The process then terminates upon powering off the automobile.

In this manner, the gas-concentration measuring apparatus 1 in this embodiment is to detect, by the window comparators 58a, 58b, 58c, whether or not there is an abnormality voltage occurrence at the connection points (terminals Vs+, COM and Ip+) of between the sensor device 10 and the sensor drive circuit 52. In the event an abnormal voltage occurs at any of the connection points, the operation mode of the sensor drive circuit 52 is switched into a protection mode, to electrically cut off between the sensor device 10 and the sensor drive circuit 52. This accordingly eliminates an abnormal current from continuously flowing through the sensor device 10, hence preventing the damage to the sensor device 10.

Meanwhile, in the gas-concentration measuring apparatus 1 in this embodiment, by energizing for a predetermined time an abnormality-identifying current required in abnormality diagnosis during an abnormality diagnosis of the sensor device 10, abnormality diagnosis can be conducted without damaging the sensor device 10.

Furthermore, in the gas-concentration measuring apparatus 1 in this embodiment, during abnormality diagnosis, the delivery of power to the heater 70 is ceased to decrease the temperature of the cells (pump cells 14 and oxygen-concentration sensing cells 24) of the sensor device 10 lower than the activation temperature thereof. As a result, the internal resistance of the cell increases. Because, in this state, flowing an abnormality-identifying current through the cells increases a potential difference between the cell electrodes, abnormality diagnosis can be done more positively than in the state the cells are at an activation temperature.

Also, in the gas-concentration measuring apparatus 1 in this embodiment, there are provided the resistance R7 and the resistance R8 which are a pull-up resistance relative to the terminal Ip+ and a pull-down resistance relative to the terminal Ip+ respectively, so as to apply a predetermined voltage (2.5V in this embodiment) to the terminal Ip+ during abnormality diagnosis. Therefore, due to high internal resistance of the cell during abnormality diagnosis, it does not happen that the voltage Ip+ become unstable even if GND short occurs on the line Vs+, thereby ensuring abnormality diagnosis. The "off" and "cut off" referred in the description include not only a perfect non-conductive state but also a state a slight current flows in a degree having no effects upon circuit operation, sensor and the like.

Although the embodiment of the invention was explained so far, the embodiment of the invention is not limited to the foregoing embodiment but can naturally take various forms as long as belonging to the technical scope of the invention.

For example, although the embodiment employed the full-range air/fuel ratio sensor as the sensor device 10, this is not limitative, i.e. it can be applied to a NOx sensor having two measurement chamber by adding another cell to the sensor device 10.

Besides, application is possible for an oxygen sensor constituted by one cell.

In the embodiment, during abnormality diagnosis, by ceasing the power delivery to the heater by rendering the duty ratio in turning on-off the heater energizing switch at 0%, the temperature of the sensor device was decreased lower than the activation temperature. However, the method of decreasing the sensor temperature lower than an activation temperature is not limited to such an approach. For example, the sensor temperature may be decreased by reducing the power delivery to the heater smaller than that of gas-concentration measurement through decreasing the on-off duty ratio of the heater energizing switch in abnormality diagnosis smaller than the duty ratio for rendering the sensor temperature to an activation temperature.

The entire disclosure of each and every foreign patent application from which the benefit of foreign priority has been claimed in the present application is incorporated herein by reference, as if fully set forth.

What is claimed is:

1. An apparatus for diagnosing an abnormality of a gas-concentration measuring apparatus, the gas-concentration measuring apparatus comprising:
   a gas sensor comprising
      a sensor device for outputting a signal commensurate with a concentration of a predetermined gas in a sample gas space, the sensor device comprising a solid electrolyte and a pair of electrodes provided on the solid electrolyte, and
      a heating section for heating the sensor device up to an activation temperature at which to output a signal commensurate with a concentration of the predetermined gas, the heating section being externally supplied with power; and
   a measuring section for measuring a concentration of the predetermined gas in the sample gas space based on an output signal of the sensor device, the measuring section being electrically connected by a plurality of electrically connecting lines to the electrodes of the sensor device of the gas sensor, the apparatus for diagnosing an abnormality of a gas-concentration measuring apparatus comprising:
   a determining section for determining whether or not voltages, on connection points between the measuring section and the sensor device, are a preset abnormal voltage value;
   a power-delivery control section for restraining a delivery of power to the heating section when a voltage, on any of the connection points, is determined as an abnormal voltage value by the determining section; and
   an abnormality diagnosing section for diagnosing an abnormality of any of the sensor device and the plurality of electrically connecting lines electrically connecting the measuring section to the electrodes of the sensor device after and while restraining a delivery of power by the power-delivery control section.

2. The apparatus for diagnosing an abnormality of claim 1, wherein the sensor device comprises: a measurement chamber communicating with the sample gas space through a diffusion resistance member; and a plurality of cells each arranged facing the measuring chamber and having a solid electrolyte and a pair of electrodes provided on the solid electrolyte,
   the measuring section is structured so as to be electrically connected to the plurality of cells of the sensor device and measure a concentration of the predetermined gas in the sample gas space based on an output signal of the plurality of cells,
   the determining section determines whether or not voltages, on connection points between the measuring section and the plurality of cells of the sensor device, are a preset abnormal value, and
   the power-delivery control section restrains a delivery of power to the heating section when a voltage, on any of the connection points, is determined as an abnormal voltage value by the determining section.

3. The apparatus for diagnosing an abnormality of claim 1, comprising:
   a current supply section for supplying a predetermined current to the sensor device through the connection points; and
   a voltage detecting section for detecting voltages on the connection points during supplying a current by the current supply section,
   wherein the abnormality diagnosing section diagnoses an abnormality by comparing between detection voltages on the connection points detected by the voltage detecting section.

4. The apparatus for diagnosing an abnormality of claim 1, wherein the power-delivery control section shuts off the delivery of power to the heating section for a predetermined time.

* * * * *